(12) United States Patent
Zhang et al.

(10) Patent No.: US 11,641,818 B2
(45) Date of Patent: May 9, 2023

(54) PHOTOPERIOD-SENSITIVE GENIC MALE STERILITY MUTANT OF UPLAND COTTON AND USE THEREOF

(71) Applicant: INSTITUTE OF COTTON RESEARCH, CHINESE ACADEMY OF AGRICULTURAL SCIENCES, Henan (CN)

(72) Inventors: Chaojun Zhang, Henan (CN); Shuli Fan, Henan (CN)

(73) Assignee: Institute of Cotton Research, Chinese Academy of Agricultural Sciences, Henan (CN)

( * ) Notice: Subject to any disclaimer, the term of this patent is extended or adjusted under 35 U.S.C. 154(b) by 267 days.

(21) Appl. No.: 16/959,401

(22) PCT Filed: Jun. 28, 2018

(86) PCT No.: PCT/CN2018/093249
§ 371 (c)(1),
(2) Date: Jun. 30, 2020

(87) PCT Pub. No.: WO2019/153627
PCT Pub. Date: Aug. 15, 2019

(65) Prior Publication Data
US 2021/0051870 A1 Feb. 25, 2021

(30) Foreign Application Priority Data

Feb. 9, 2018 (CN) .......................... 201810132189.8

(51) Int. Cl.
*A01H 6/60* (2018.01)
*A01H 3/02* (2006.01)
*A01H 1/02* (2006.01)
*A01H 5/10* (2018.01)

(52) U.S. Cl.
CPC ................ *A01H 3/02* (2013.01); *A01H 1/02* (2013.01); *A01H 5/10* (2013.01); *A01H 6/604* (2018.05)

(58) Field of Classification Search
CPC ..................................................... A01H 6/604
See application file for complete search history.

(56) References Cited

U.S. PATENT DOCUMENTS 4,570,380 A * 2/1986 Ray .......................... A01H 1/02
800/274
5,981,833 A 11/1999 Wise et al.

OTHER PUBLICATIONS

Ma et al Journal of Integrative Plant Biology vol. 55, No. 7, pp. 608-618 (Year: 2013).*
Zhang, Meng et al., "Genetic Analysis and Preliminary Mapping of the Photoperiod-Sensitive Male Sterility Gene ys-1 in Upland Cotton," J. Cotton Sci., 2017, 29(1), pp. 9-16.

* cited by examiner

*Primary Examiner* — David H Kruse
(74) *Attorney, Agent, or Firm* — Don D. Cha; HDC Intellectual Property Law, LLP

(57) ABSTRACT

The present invention provides use of a photoperiod-sensitive genic male sterility mutant of cotton in crossbreeding or hybrid seed production. The fertility of the photoperiod-sensitive genic male sterility mutant of cotton is influenced by the photoperiod. The photoperiod characteristic of the photoperiod-sensitive genic male sterility mutant of cotton is that, the photoperiod-sensitive genic male sterility mutant of cotton shows normal fertility when the illumination time is shorter than 11.5 h and shows genic male sterility when the illumination time is longer than 12 h; the photoperiod-sensitive genic male sterility mutant of cotton is in a fertility change period when the illumination time is in a range of 11.5-12 h and has less pollen. The photoperiod-sensitive genic male sterility mutant of cotton is PSM1, and/or a photoperiod-sensitive genic sterile line obtained through selective breeding of hybridized and/or backcrossed and/or self-bred offsprings of the PSM1.

9 Claims, 4 Drawing Sheets

PHOTOPERIOD-SENSITIVE GENIC MALE STERILITY MUTANT OF UPLAND COTTON AND USE THEREOF

CROSS-REFERENCE TO RELATED APPLICATIONS

This application is a U.S. national stage application, filed under 35 U.S.C. § 371, of PCT Patent Application No. PCT/CN2018/093249, filed Jun. 28, 2018, entitled "PHOTOPERIOD-SENSITIVE GENIC MALE STERILITY MUTANT OF UPLAND COTTON AND USE THEREOF," which claims the priority benefit of Chinese Patent Application No. 201810132189.8, filed Feb. 9, 2019.

FIELD OF THE INVENTION

The present invention belongs to the technical field of hybridization and seed production in agriculture, and in particular relates to a photoperiod-sensitive genic male sterility mutant of upland cotton PSM1, and use thereof.

BACKGROUND OF THE INVENTION

To avoid artificial emasculation, sterile lines are the most effective way to for hybrid seed production. Male sterile lines of cotton mainly fall into two types: cytoplasmic male sterile lines and genic sterile lines. The genic male sterile lines overcome the defect of cytoplasmic influence and thus have a greater utility value. The male sterile material of the present invention belongs to the genic male sterile line. Because fertility is influenced by a photoperiod, seed production can be conducted through a two-line method without a maintainer line, which is the most economical and effective hybrid seed production method by utilizing the sterile line.

In the 1960s, Meyer et al. bred cytoplasmic male sterile lines of upland cotton from cytoplasms of *Gossypium arboreum* L., *Gossypium anomalum* and *Gossypium harknessii* through distant hybridization, and found two restorer lines of *Gossypium harknessii*, thereby successfully realizing three-line combination. Cytoplasmic male sterile lines of cotton are classified into cytoplasmic sterile lines of *Gossypium harknessii* (D2-2), cytoplasmic sterile lines of *Gossypium arboreum* L. (A2), cytoplasmic sterile lines of *Gossypium anomalum* (B1), cytoplasmic sterile lines of *Gossypium trilobum* (D8), cytoplasmic sterile lines of upland cotton (AD1) and cytoplasmic sterile lines of *Gossypium barbadense* L. (AD2). The genotypes of restorer lines are mainly Rf1 and Rf2. The Rf1 gene not only can restore the fertility of CMS-D2, but also can restore the fertility of CMS-D8, while the Rf2 can only restore the fertility of CMS-D8. Also, the Rf2-linked SSR marker site is found.

Many types of genic male sterile lines of cotton have been found. Up to now, 17 different types of genic sterile lines have been found, including 9 recessive genic sterile lines, namely ms1, ms2, ms3, ms5ms6, ms8ms9, ms13, ms14, ms15 and ms16; and 8 dominant genic sterile lines of Ms4, Ms7, Ms10, Ms11, Ms12, Ms17, Ms18 and Ms19 respectively. Among the 17 sterile lines, 12 are found in the upland cotton and 5 are found in the *Gossypium barbadense* L.; ms2 and Ms4 are completely sterile, ms1 and ms3 are only partially sterile, and ms8ms9 show anther indehiscence. The cotton thermo-sensitive male sterile line Temian S-1 bred by Hunan Agricultural University is presented as sterile when the average daily temperature is higher than 27° C. Zhang Tianzhen et al. have bred Dong81A male sterile lines marked with virescent cotyledon, such that fertile plants can be removed from the field by means of the cotyledon leaf color performance, and thus sterile plants are leaved for production of hybrid seeds. The Zhong9106 virescent photoperiod-sensitive male sterile line material of upland cotton bred by Institute of Cotton Research of Chinese Academy of Agricultural Sciences through a space-flight mutation breeding technology, is presented as sterile when growing under long-day conditions with a photoperiod of 13 to 14.5 hours, and is presented as fertile when growing under short-day conditions with a photoperiod of 11 to 12.5 hours and an average daily temperature of 21.5° C. or higher (ZL 2011 1 0294545.4). Virescent, as an obvious indicator trait, plays an important role in genetic breeding. The virescent mutant can be used as a marker trait to eliminate plants affecting seed purity at the seedling stage, which not only can simplify the breeding process of improved varieties, but also can improve the seed purity. In recent years, both breeders and basic researchers have paid more and more attention to leaf color mutants.

A virescent mutant of plant is a leaf color mutant that is yellowed at the seedling stage or early stage of growing point and turns green along with the growth of the plant. The virescent mutation can be found in many flowering plants. Most homozygous virescent mutants appear obviously at the seedling stage, the cotyledons or euphylla are presented with different degrees of yellow colors, and turn green at the flowering stage or full-bloom stage. The virescent mutation is different from a general chlorophyll deletion mutant. The virescent mutation is presented obviously and can be identified at the seedling stage, and most of the mutations are simple in inheritance and have little or no effect on the yield. Therefore, it can be used as a marker trait in the breeding to simplify the breeding procedure of improved varieties. The method of combining leaf color mutation with male sterility can effectively ensure the purity of hybrid seeds. The photo-sensitive male sterile line of rice XinguangS carrying a green-revertible yellow leaf marker has been cultivated in rice. In the utilization of cotton heterosis, the virescent marker has also been paid attention by cotton breeders. The cotton virescent mutant is also usually presented with yellow new leaves. With the development of leaves, the color turns green gradually, and the trait is easy to identify. Therefore, it is an ideal experimental material for identifying cotton gene linkage groups, homeosis groups and mapping of cotton mutant genes.

SUMMARY OF THE INVENTION

An objective of the present invention is to provide a photoperiod-sensitive genic male sterility mutant of cotton and use thereof.

The male fertility of the photoperiod-sensitive genic male sterility mutant of cotton provided by the present invention is influenced by photoperiod. The photoperiod refers to the alternations of a light period and a dark period in the changing of a day-night cycle. Photoperiodism is the physiological reaction of organisms to the length of night or a dark period. The photosensitivity of the photoperiod-sensitive genic male sterility mutant of cotton refers to photoperiod sensitivity. The duration of the light period in the day-night cycle is described in meteorology as the hours of sunshine, i.e., the time from sunrise to sunset. The duration of the corresponding dark period is not specifically described herein, and is obtained by subtracting the hours of sunshine from 24 hours. The photoperiods mentioned herein are all photoperiods under natural conditions, and the hours of sunshine are also the concept of hours of sunshine in meteorology. The photoperiod-sensitive genic male sterility mutant of cotton in the present invention can also be influenced by artificially controlled photoperiods, and the influence effect is the same as that of the natural photoperiods.

In a first aspect, the present invention provides use of photoperiod-sensitive genic male sterility mutant of cotton in hybridization and/or seed production.

Correspondingly, the present invention provides a hybridization and/or seed production method. The method includes the following steps: conducting hybridization and/or seed production by utilizing the photoperiod-sensitive genic male sterility mutant of cotton.

The fertility of the photoperiod-sensitive genic male sterility mutant of cotton is influenced by the photoperiod. The photoperiod-sensitive genic male sterility mutant of cotton shows normal fertility (normal pollen can be developed) when the daily illumination time is less than 11.5 h, shows genic male sterility (no normal pollen can be developed) when the daily illumination time is greater than 12 h, and is in a fertility change period when the daily illumination time is in the range of 11.5-12 h. The development of female gametes is not influenced by the photoperiod. That is, the females all show fertility.

Further, the photoperiod-sensitive genic male sterility mutant of cotton photoperiod-sensitive genic male sterility mutant carries a prophyll yellowing selection marker.

Furthermore, for the photoperiod-sensitive genic male sterility mutant of cotton carrying the prophyll yellowing selection marker, its prophyll yellowing trait is affected by temperature and illumination intensity. Under high light intensity and/or low temperature conditions, the prophyll tends to yellow.

Further, the male sterility is embodied in that: after the pollen grains develop to a mid-late uninucleate stage, the pollen grains cannot finally mature rather than the tapetal layer being degraded in advance since a tapetal layer cannot provide outer-layer materials to a pollen wall.

Furthermore, the male sterility trait displayed by the photoperiod-sensitive genic male sterility mutant of cotton is a single gene recessive trait. The prophyll yellowing trait displayed by the photoperiod-sensitive genic male sterility mutant of cotton carrying the prophyll yellowing selection marker is a recessive trait, and is incompletely linked with the male sterile trait.

More specifically, in the embodiments of the present invention, the photoperiod-sensitive genic male sterility mutant of cotton carrying the prophyll yellowing selection marker is a mutant PSM1 obtained through genetic variation caused by somatic tissue culture regeneration of a upland cotton strain W10 (the high-differentiation-rate strain W10 screened out from CRI24). The adopted cotton tissue culture system is the tissue culture system mentioned in the Chinese patent ZL200610089439.1 proposed by Zhang Chaojun et al., and the adopted explant is a hypocotyl tissue of W10 aseptic seedling. Compared with the upland cotton strain W10, the finally obtained PSM1 has no difference in growth and development rules and field growth vigour with W10 when planted in the test field of south testing ground of the Institute of Cotton Research of Chinese Academy of Agricultural Sciences in Anyang, Henan Province, except for phenotypic traits such as the photoperiod-sensitive male sterility trait and the prophyll yellowing trait.

The preservation number of the mutant PSM1 in the China General Microbiological Culture Collection Center is CGMCC No. 14613.

Furthermore, the photoperiod-sensitive genic male sterility mutant of cotton can also be an improved cotton material in which the prophyll yellowing selection marker of the photoperiod-sensitive genic male sterility mutant of cotton carrying the prophyll yellowing selection marker described above is modified into other selection markers or no selection markers, but the photoperiod-sensitive genic male sterile trait can still be maintained.

In a second aspect, the present invention provides a method for selective breeding of photoperiod-sensitive genic male sterile cotton materials.

The method for selective breeding of photoperiod-sensitive genic male sterile cotton materials provided by the present invention can specifically be any of the following.

Method 1, including the following steps: hybridizing the photoperiod-sensitive genic male sterility mutant of cotton as described in any preceding paragraph with another cotton material to obtain a F1 generation, and selecting cotton materials with the photoperiod-sensitive genic male sterile trait from the offspring population of the F1 generation.

Further, as desired, the cotton materials with the photoperiod-sensitive genic male sterile trait selected from the offspring population of the F1 generation are subjected to one or more selfings, and the cotton materials with the photoperiod-sensitive genic male sterile trait are selected from the offspring of selfing.

Method 2, including the following steps: transferring the photoperiod-sensitive genic male sterile trait of the photoperiod-sensitive genic male sterility mutant of cotton as described in any preceding paragraph or the cotton material with the photoperiod-sensitive genic male sterile trait as obtained in the method A to another cotton material through backcrossing, and selecting the cotton material with the photoperiod-sensitive genic male sterile trait from the offspring of backcrossing.

In a third aspect, the present invention also provides a hybrid seed production method.

The hybrid seed production method as provided by the present invention specifically includes the following steps: conducting hybridizing by using the photoperiod-sensitive genic male sterility mutant of cotton described in any preceding paragraph or a cotton material with the photoperiod-sensitive genic male sterile trait selected by the "method for selective breeding of photoperiod-sensitive genic male sterile cotton materials" described above as a female parent and using a fertile cotton material as a male parent, so as to obtain hybrid seeds.

In a fourth aspect, the present invention also provides a hybridization method.

The hybrid seeds obtained by using the aforementioned "hybrid seed production method" are used for entering the hybridization program, so as to select a photoperiod-sensitive male sterile line and/or breed a new cotton variety.

In a fifth aspect, the present invention also provides a method for establishing a mass selection-mass hybridization system of cotton.

The method for establishing a mass selection-mass hybridization system of cotton provided by the present invention specifically includes the following steps:
(a) conducting mixed planting of cotton materials with a photoperiod-sensitive genic male sterile trait and one, two or more other fertile cotton materials under a condition that the daily illumination time is greater than 11.5 h, mixed crossing and pollinating, and harvesting seeds on sterile plants, so as to obtain mixed hybrid seeds;

(b) planting the hybrid seeds obtained in the step (a) under a condition that the daily illumination time is greater than 11.5 h, wherein the hybrid seeds are all fertile plants; subjecting the plants to selfing or natural pollination and boll setting as normal cotton; harvesting single plants or mixed plants and planting continually, such that trait segregation occurs in this generation; separating sterile plants, and marking photosensitive-sterile plants; and then conducting b1) or b2);

b1) subjecting the fertile plants to selfing or natural pollination and boll setting, and selecting desired individual fertile plants from the offspring to breed a new cotton variety; and conducting step b2) on the individual sterile plants in the offspring;

b2) mixed crossing and pollinating the sterile plants and one, two or more other fertile cotton materials, and harvesting seeds on the sterile plants.

Further, the method also includes a step (c) after the step (b):

(c) planting the seeds on the sterile plants as harvested in the step b2) under a condition that the daily illumination time is greater than 11.5 h, and then repeating the step (b) for one or more times.

Still further, the method also includes a step (d) after the step (c):

(d) mixing multiple fertile individual plants selected in multiple steps (b1) and then taking the mixture as a mixed-line material to breed a mixed-line new cotton variety.

The cotton material with the photoperiod-sensitive genic male sterile trait is any one or more of the photoperiod-sensitive genic male sterility mutant of cotton described in any preceding paragraph and a cotton material with the photoperiod-sensitive genic male sterile trait selected by the "method for selective breeding of photoperiod-sensitive genic male sterile cotton materials" described above.

In this method, all of the materials carrying recessive photoperiod-sensitive genic sterile genes in the hybrid seeds obtained in each stage and offspring thereof, can be used for the aforementioned "method for selective breeding of photoperiod-sensitive genic male sterile cotton materials", and further the photoperiod-sensitive genic male sterile cotton materials are selected.

In a sixth aspect, the present invention also claims upland cotton PSM1 (*Gossypium hirsutum* L.), of which the preservation number in the China General Microbiological Culture Collection Center is CGMCC No. 14613.

Description of Preservation
Plant Name: upland cotton
Latin Name: *Gossypium hirsutum* L.
The referenced Biological material (strain): PSM1
Preservation Institution: China General Microbiological Culture Collection Center
Short Name of Preservation Institution: CGMCC
Address: No. 3, Yard No. 1, Beichen West Road, Chaoyang District, Beijing
Date of Preservation: Jan. 8, 2018
Registration number in the Collection center: CGMCC No. 14613
The deposit was made and accepted under the terms of the Budapest Treaty.

DETAILED DESCRIPTION OF THE INVENTION

The following examples facilitate a better understanding of the present invention, but do not limit the present invention. The experimental methods in the following examples are conventional methods, unless otherwise specified. The experimental materials used in the following examples were purchased from conventional biochemical reagent companies, unless otherwise specified. In the quantitative experiments of the following examples, triplicate experiments are set up, and the results are averaged.

Cotton strain W10: a high-differentiation-rate strain W10 suitable for cotton tissue culture, is screened out from CRI24, and is recorded in the article "Zhang Chaojun. Establishment of High Frequency Regeneration System and Genetic Analysis for Mature Leaf Petioles in Upland Cotton (*G. Hirsutum* L.). Chinese Academy of Agricultural Sciences, 2008 Doctoral Thesis". This article is available to the public from the applicant and can only be used for reproducing the experiment of the present invention.

Example 1: Obtaining and Trait Identifying of Photoperiod-Sensitive Genic Male Sterility Mutant of Upland Cotton PSM1

I. Obtaining of Photoperiod-Sensitive Genic Male Sterility Mutant of Upland Cotton PSM1

W10 came from the transgenic research and application project of the Institute of Cotton Research of Chinese Academy of Agricultural Sciences. It was a high-differentiation-rate strain screened out from CRI24 and suitable for cotton tissue culture. The W10 tissue culture system proposed by Zhang Chaojun (ZL200610089439.1) was adopted as the cotton tissue culture system. Since the establishment of the cotton tissue culture technology by Zhang Chaojun in 2006, the creation of cotton mutants has been focused on. The hypocotyl tissue of W10 aseptic seedlings were cultured to obtain a large number of regenerated plants, from which the photoperiod-sensitive genic male sterile mutants were selected. In 2012, a male sterile mutant plant was found in the third generation population of the same regenerated cotton plant. The male sterile mutant plant was grafted to Sanya, Hainan, and was found to be fertile in winter and sterile in summer, and was named PSM1 (Photoperiod-sensitive genic male Sterility Mutant of upland cotton).

The male sterile mutant PSM1 had been deposited in China General Microbiological Culture Collection Center (referred to CGMCC for short, address: No. 3, Yard No. 1, Beichen West Road, Chaoyang District, Beijing) on Jan. 8, 2018, had the suggested classification name of *Gossypium hirsutum* L., and had a collection center registration number of CGMCC No. 14613.

Figure 1:
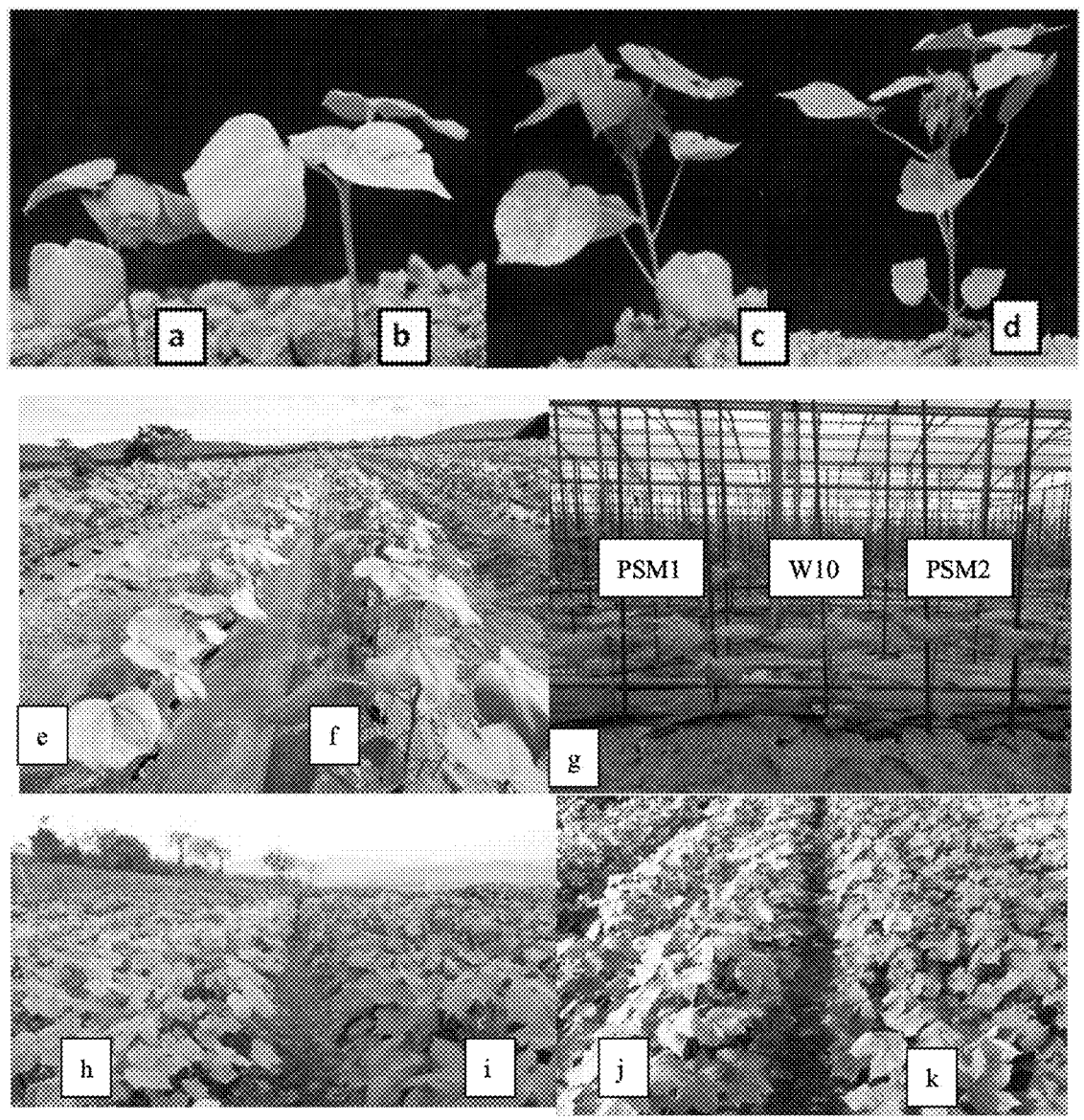
FIG. 1 shows the field phenotypes of PSM1 and PSM4 at the seedling stage in Anyang, Henan and field phenotypes of PSM1, PSM2, PSM3 and PSM4 at the flowering stage in Sanya, Hainan. a: W10 prophyll unfold phase, with normal leaf color; b: PSM1 prophyll unfold phase, with larger cotyledons and yellowed prophyll; c: the five-leaf phase of PSM1 normally sown in Anyang, Henan, with yellowed prophyll; d: the five-leaf phase of W10 normally sown in Anyang, Henan, with normal leaf color; e: yellowed PSM1 sown in Sanya, Hainan; f: the seedling stage of PSM4 sown in field of Sanya, Hainan, and g: PSM1, PSM2, and W10 sown in a greenhouse of Sanya, Hainan. h: the flowering stage of PSM1 sown in field of Sanya, Hainan, i: the flowering stage of PSM4 sown in field of Sanya, Hainan, j: the flowering stage of PSM2 sown in field of Sanya, Hainan, and k: flowering stage of PSM3 sown in field of Sanya, Hainan.
Figure 2:
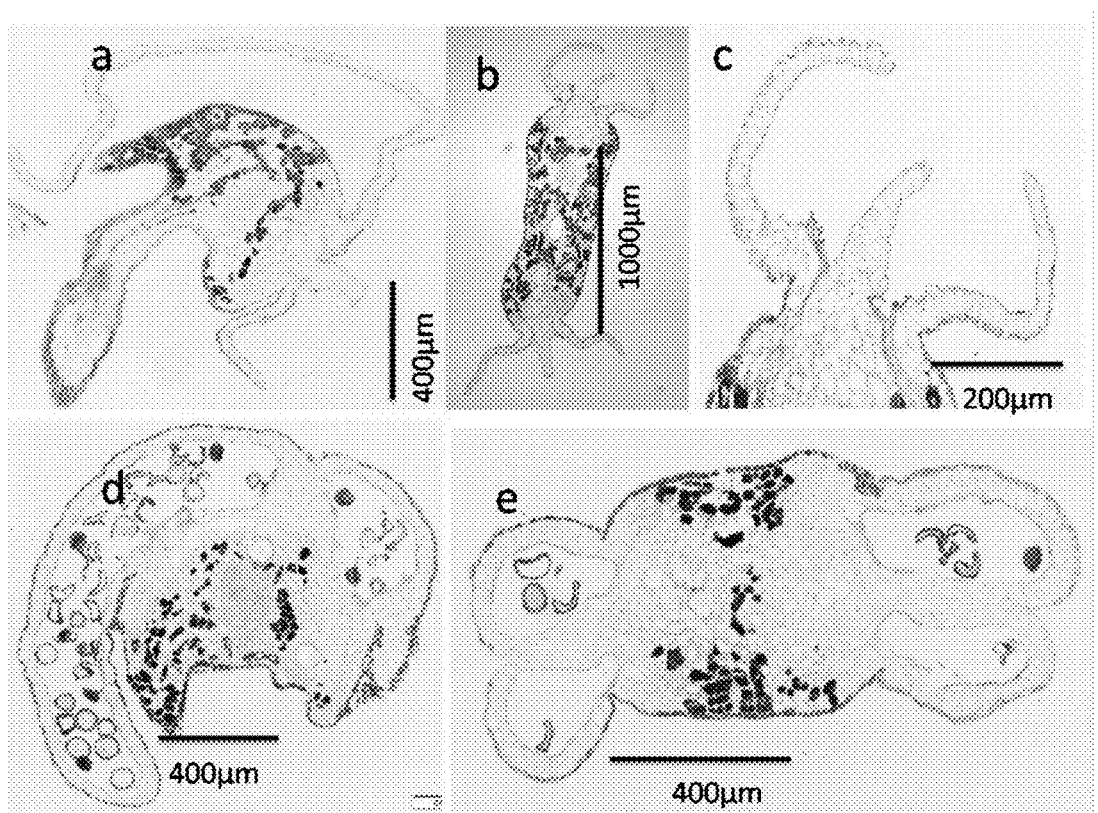
FIG. 2 shows indehiscent anther of PSM1. a: longitudinal section of dehiscent anther of W10; b: lateral section of dehiscent anther of W10; c: lateral section of dehiscent anther chamber of W10; dehiscent pollen chambers can be seen in the 3 pictures of a, b and c, after the manufacturing process of paraffin sectioning, all pollen grains are eluted by liquid; d: longitudinal section of anther of PSM1; e: lateral section of another of PSM1; in the two pictures of d and e, it can be seen that the pollen chamber is not dehiscent, and there are still residual abnormally-developed pollen grains.

II. Trait Identification of Photoperiod-Sensitive Genic Male Sterility Mutant PSM1 of Cotton 1. The phenotype of PSM1 was different from each of those of the reported cotton virescent mutants, and belonged to a new type. The PSM1 mutant was planted in a field of Anyang, Henan. When it was sown in the middle and late April, the cotyledons were presented as green, but slightly yellower and larger than that of W10, the prophyll (the first and second euphyllas) was yellowed, and the yellowing could not be recovered. Thereafter, the euphyllas were all green without the yellowing phenomenon. In Anyang, Henan, no yellowing phenomenon was observed when seedling was conducted in a greenhouse or seed sowing was conducted in late May. When the seeds are directly sowed in a field of Sanya, Hainan, the plants were presented with whole plant yellowing. The plants had serious yellowing at the seedling stage, and turned yellow-green at the flowering and boll setting stage, and the flowering stage of the plants were 2-3 days later than that of W10 under the yellowing condition. When the seeds were sowed in a greenhouse of Hainan, the plants had no yellowing phenomenon. Therefore, according to preliminary tests, it was believed that yellowing is related to light intensity and temperature. The plants were easily yellowed under high light intensity and low temperature conditions. Referring to FIGS. 1 and 2, 2. PSM1 was planted in Sanya to observe the changes of fertility. Cotton is a perennial plant in Hainan. It can be observed for many years once planted. After consecutive 2 years of observation of the fertility change of PSM1 from sowing in May 2014 to May 2016, it was found that pollen began to appear in PSM1 about November 15, and it could be subjected to selfing and boll setting and entered the fertile stage. Till February 25 to March 1 of the following year, the phenomenon of anther indehiscence, no pollen grains on the anther, and selfing without boll setting began to appear, and thus it entered the male sterility stage. The selfing and boll setting of PSM1 occurred from late November of each year to early March of the following year, and thus it could be inferred that normal anther development might occur in late October, and normal anther development will be kept to early February of the following year. In late February of the following year, it began to abort. As could be seen from FIG. 4, pollen grain abortion of PSM1 is caused by the fact that the tapetal layer cannot provide fillings to the outer layer of the pollen wall after the mid-late uninucleate stage. It took about 10-15 days from the mid-late uninucleate stage to the flowering stage. According to the hours of sunshine of the 10-15 days that were deduced back according to the fertility change phase, it is inferred that the photoperiod of fertility change of PSM1 is about 11.5 hours of illumination time/12.5 hours of dark time (Table 1). Females were fertile throughout the year and were not affected by the photoperiod. The fertility of the PSM1 mutant was controlled by the hours of sunshine and has no obvious relationship with light intensity. There was no experimental data supporting that the fertility was influenced by temperature.

TABLE 1

The duration of day in Jiyang town, Sanya city, Hainan province during the fertility change period of PSM1

| Date | Sunrise | Sunset | Daylength |
|---|---|---|---|
| The hours of sunshine during the transformation from male sterility to fertility in 2015 | | | |
| October 30th | 6:40:10 AM | 6:10:34 PM | 11:30:24 AM |
| October 31st | 6:40:34 AM | 6:10:04 PM | 11:29:30 AM |
| November 1st | 6:40:59 AM | 6:09:34 PM | 11:28:35 AM |
| November 2nd | 6:41:24 AM | 6:09:06 PM | 11:27:42 AM |
| November 3rd | 6:41:50 AM | 6:08:39 PM | 11:26:49 AM |
| November 4th | 6:42:17 AM | 6:08:13 PM | 11:25:56 AM |
| November 5th | 6:42:43 AM | 6:07:48 PM | 11:25:05 AM |
| November 6th | 6:43:11 AM | 6:07:24 PM | 11:24:13 AM |
| November 7th | 6:43:39 AM | 6:07:02 PM | 11:23:23 AM |
| November 8th | 6:44:07 AM | 6:06:40 PM | 11:22:33 AM |
| November 9th | 6:44:50 AM | 6:06:38 PM | 11:21:48 AM |
| November 10th | 6:45:20 AM | 6:06:19 PM | 11:20:59 AM |
| November 11th | 6:45:50 AM | 6:06:01 PM | 11:20:11 AM |
| November 12th | 6:46:20 AM | 6:05:44 PM | 11:19:24 AM |
| November 13th | 6:46:51 AM | 6:05:29 PM | 11:18:38 AM |
| November 14th | 6:47:22 AM | 6:05:14 PM | 11:17:52 AM |
| November 15th | 6:47:54 AM | 6:05:01 PM | 11:17:07 AM |
| November 16th | 6:48:27 AM | 6:04:50 PM | 11:16:23 AM |
| November 17th | 6:48:59 AM | 6:04:39 PM | 11:15:40 AM |
| November 18th | 6:49:33 AM | 6:04:30 PM | 11:14:57 AM |
| November 19th | 6:50:06 AM | 6:04:22 PM | 11:14:16 AM |
| November 20th | 6:50:40 AM | 6:04:15 PM | 11:13:35 AM |
| November 21st | 6:51:14 AM | 6:04:10 PM | 11:12:56 AM |
| November 22nd | 6:51:49 AM | 6:04:06 PM | 11:12:17 AM |
| November 23rd | 6:52:24 AM | 6:04:03 PM | 11:11:39 AM |
| November 24th | 6:52:59 AM | 6:04:01 PM | 11:11:02 AM |
| November 25th | 6:53:34 AM | 6:04:01 PM | 11:10:27 AM |
| November 26th | 6:54:10 AM | 6:04:02 PM | 11:09:52 AM |
| November 27th | 6:54:46 AM | 6:04:04 PM | 11:09:18 AM |

TABLE 1-continued

The duration of day in Jiyang town, Sanya city, Hainan province during the fertility change period of PSM1

| Date | Sunrise | Sunset | Daylength |
|---|---|---|---|
| November 28th | 6:55:22 AM | 6:04:08 PM | 11:08:46 AM |
| November 29th | 6:55:58 AM | 6:04:12 PM | 11:08:14 AM |

The hours of sunshine during the transformation from fertility to male sterility in 2016

| Date | Sunrise | Sunset | Daylength |
|---|---|---|---|
| February 10th | 7:11:44 AM | 6:40:01 PM | 11:28:17 AM |
| February 11th | 7:11:18 AM | 6:40:29 PM | 11:29:11 AM |
| February 12th | 7:10:50 AM | 6:40:57 PM | 11:30:07 AM |
| February 13th | 7:10:22 AM | 6:41:24 PM | 11:31:02 AM |
| February 14th | 7:09:52 AM | 6:41:50 PM | 11:31:58 AM |
| February 15th | 7:09:22 AM | 6:42:16 PM | 11:32:54 AM |
| February 16th | 7:08:51 AM | 6:42:42 PM | 11:33:51 AM |
| February 17th | 7:08:19 AM | 6:43:07 PM | 11:34:48 AM |
| February 18th | 7:07:45 AM | 6:43:31 PM | 11:35:46 AM |
| February 19th | 7:07:11 AM | 6:43:55 PM | 11:36:44 AM |
| February 20th | 7:06:37 AM | 6:44:18 PM | 11:37:41 AM |
| February 21st | 7:06:01 AM | 6:44:41 PM | 11:38:40 AM |
| February 22nd | 7:05:24 AM | 6:45:04 PM | 11:39:40 AM |
| February 23rd | 7:04:47 AM | 6:45:26 PM | 11:40:39 AM |
| February 24th | 7:04:09 AM | 6:45:47 PM | 11:41:38 AM |
| February 25th | 7:03:30 AM | 6:46:08 PM | 11:42:38 AM |
| February 26th | 7:02:51 AM | 6:46:29 PM | 11:43:38 AM |
| February 27th | 7:02:11 AM | 6:46:49 PM | 11:44:38 AM |
| February 28th | 7:01:30 AM | 6:47:09 PM | 11:45:39 AM |
| February 29th | 7:00:48 AM | 6:47:28 PM | 11:46:40 AM |
| March 1st | 7:00:06 AM | 6:47:47 PM | 11:47:41 AM |
| March 2nd | 6:59:24 AM | 6:48:05 PM | 11:48:41 AM |
| March 3rd | 6:58:40 AM | 6:48:23 PM | 11:49:43 AM |
| March 4th | 6:57:57 AM | 6:48:41 PM | 11:50:44 AM |
| March 5th | 6:57:12 AM | 6:48:58 PM | 11:51:46 AM |
| March 6th | 6:56:28 AM | 6:49:15 PM | 11:52:47 AM |
| March 7th | 6:55:42 AM | 6:49:32 PM | 11:53:50 AM |
| March 8th | 6:54:57 AM | 6:49:48 PM | 11:54:51 AM |
| March 9th | 6:54:10 AM | 6:50:04 PM | 11:55:54 AM |
| March 10th | 6:53:24 AM | 6:50:20 PM | 11:56:56 AM |
| March 11th | 6:52:52 AM | 6:50:52 PM | 11:58:00 AM |

Note:
Nov. 15, 2015 to Nov. 25, 2015 and Feb. 25, 2016 to Mar. 1, 2016 are the fertility change period. The data of hours of sunshine (i.e. the day length in Table 1) are derived from richurimo.51240.com/.

The progeny of PSM1 was planted in a field of Sanya, Hainan, and progeny materials with different yellowing degrees could be separated. The progeny materials were named PSM1, PSM2, PSM3 and PSM4 (FIG. 1) according to the yellowing degrees from moderate to light, wherein PSM4 had no yellowing trait. The progeny materials all maintained the photoperiod-sensitive sterility characteristic of PSM1. In Anyang, The PSM2 and PSM3 with less yellowing degrees in Sanya, Hainan and the PSM4 with no yellowing trait in Sanya, Hainan had no prophyll yellowing phenotype, but still retained the photoperiod-sensitive male sterility of PSM1. Therefore, PSM1 could be used to breed photoperiod-sensitive genic male sterile materials bearing no yellowing markers.

Figure 3:
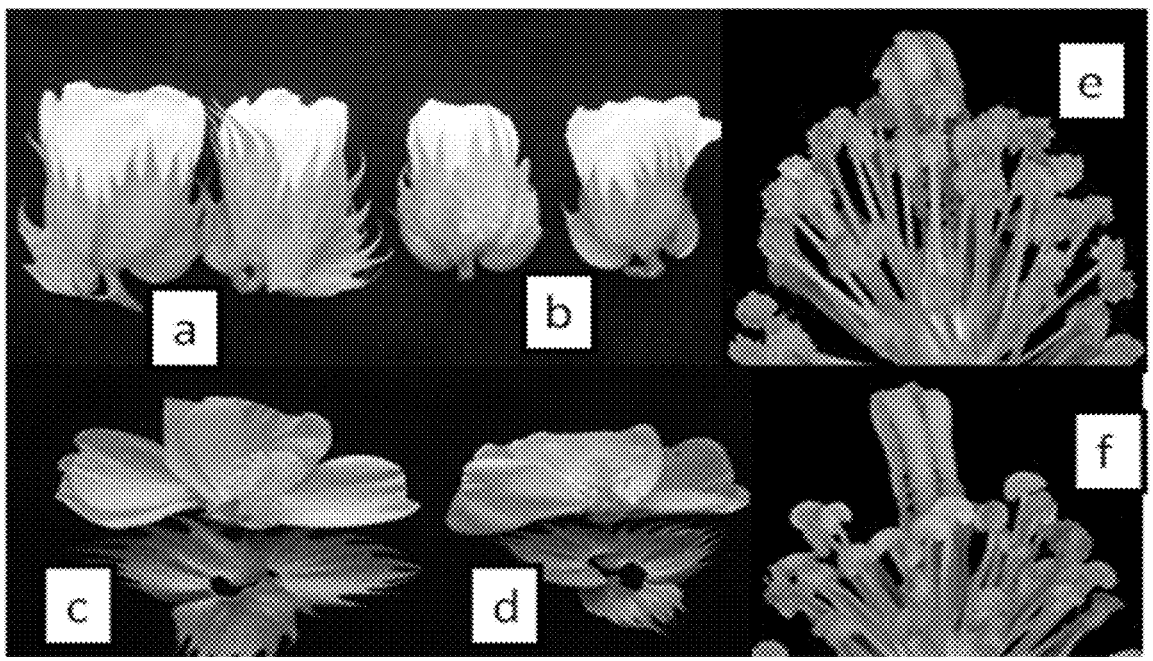
FIG. 3 shows the flower of the PSM1 photoperiod-sensitive male sterile line. a: the flower on the blooming day of W10, b: the flower on the blooming day of PSM1, slightly smaller than that of W10; c: the flower on the blooming day of W10, with the stigma being lower than the anther; d: the flower on the blooming day of PSM1, with the stigma being lower than the anther, like that of W10; e: the stamen on the second day of blooming of W10, with the stigma being slightly higher than the anther, and a large number of pollen grains can be seen on the anther; f: the stamen on the second day of blooming of PSM1, with the stigma being slightly higher than the anther like that of W10, but the anther is not dehiscent, and there are still no pollen grains on the anther.

3. When planted in a field of Anyang, the PSM1 mutants all exhibited as having flowers slightly smaller than those of W10, and the anthers of them were not dehiscent. The sections showed that the pollen grains therein were wizened and there was no outer wall of pollen grains (FIG. 2). The stigmas of them were the same as those of normal cotton, and there was no phenomenon of stigma elongation on the day of flowering (FIG. 3). In particular, when the PSM1 mutants were planted in Anyang, Henan in 2017 with the condition that there was no direct sunlight during the more than 20 consecutive days of cloudy and rainy weather in middle and late July in Anyang, Henan (Table 2), more than 3,500 selfings were done, and there was no selfing boll. The observation under a microscope showed that the anthers were not dehiscent, and the sections showed no normal pollen grains. Therefore, the photoperiod-sensitive genic male sterility of the mutant was not affected by long-term cloudy and rainy weather.

TABLE 2

Weather Conditions in Anyang, Henan from July to August in 2017 (Data Source: weather.mipang.com/)

| | Highest temperature in ° C. | Lowest temperature in ° C. | Weather |
|---|---|---|---|
| July | | | |
| 1. | 35. | 24. | Cloudy |
| 2. | 35. | 24. | Sunny |
| 3. | 37. | 26. | Sunny |
| 4. | 38. | 25. | Cloudy |
| 5. | 35. | 22. | Cloudy turned to light rain |
| 6. | 29. | 23. | Heavy rain turned to overcast |
| 7. | 35. | 25. | Cloudy turned to sunny |
| 8. | 39. | 26. | Sunny |
| 9. | 35. | 25. | Cloudy turned to sunny |
| 10. | 38. | 25. | Cloudy turned to sunny |
| 11. | 39. | 26. | Sunny |
| 12. | 37. | 26. | Sunny |
| 13. | 37. | 26. | Cloudy |
| 14. | 36. | 25. | Thundershower turned to light rain |
| 15. | 30. | 23. | light rain turned to shower |
| 16. | 31. | 24. | Cloudy turned to shower |
| 17. | 32. | 25. | Shower turned to light rain |
| 18. | 33. | 25. | light rain turned to shower |
| 19. | 33. | 27. | Sunny |
| 20. | 35. | 27. | Cloudy turned to sunny |
| 21. | 35. | 23. | Shower turned to thundershower |
| 22. | 31. | 26. | Cloudy |
| 23. | 34. | 25. | Cloudy |
| 24. | 31. | 24. | Cloudy turned to shower |
| 25. | 30. | 25. | Cloudy |
| 26. | 32. | 22. | Thundershower |
| 27. | 25. | 20. | Shower |
| 28. | 26. | 20. | Shower |
| 29. | 23. | 19. | Shower turned to overcast |
| 30. | 27. | 21. | Overcast turned to cloudy |
| 31. | 30. | 24. | Cloudy turned to shower |
| August | | | |
| 1. | 29. | 24. | Shower turned to heavy rain |
| 2. | 28. | 23. | Moderate rain turned to cloudy |
| 3. | 34. | 25. | Sunny |
| 4. | 36. | 26. | Sunny |
| 5. | 35. | 26. | Sunny turned to cloudy |
| 6. | 36. | 25. | Thundershower turned to cloudy |
| 7. | 33. | 24. | Cloudy |
| 8. | 35. | 23. | Sunny turned to cloudy |
| 9. | 33. | 22. | Sunny |
| 10. | 35. | 24. | Sunny |
| 11. | 35. | 24. | Sunny turned to cloudy |
| 12. | 29. | 22. | Shower |
| 13. | 30. | 22. | Cloudy turned to sunny |
| 14. | 31. | 22. | Sunny |
| 15. | 32. | 23. | Sunny |
| 16. | 33. | 23. | Cloudy |
| 17. | 30. | 22. | Cloudy |
| 18. | 28. | 23. | Shower |
| 19. | 27. | 23. | light rain turned to overcast |
| 20. | 30. | 23. | Cloudy turned to sunny |
| 21. | 33. | 23. | Cloudy |
| 22. | 31. | 24. | Cloudy turned to light rain |
| 23. | 31. | 24. | Shower turned to overcast |
| 24. | 34. | 24. | Sunny turned to cloudy |
| 25. | 28. | 20. | overcast turned to light rain |
| 26. | 27. | 20. | Cloudy turned to overcast |
| 27. | 24. | 19. | Overcast |
| 28. | 23. | 16. | light rain turned to overcast |
| 29. | 21. | 15. | Moderate rain |
| 30. | 21. | 16. | Cloudy |
| 31. | 26. | 17. | Cloudy |

4. The flowers of the PSM1 mutant in Hainan from the end of middle November to the late February of the following year were similar to those of W10. The anther indehiscence could occur normally, the pollen vitality is normal, and selfing and boll setting could happen. The anthers did not dehisce in other months, the stigmas were developed normally, and hybridization and boll setting could occur.

Figure 4:
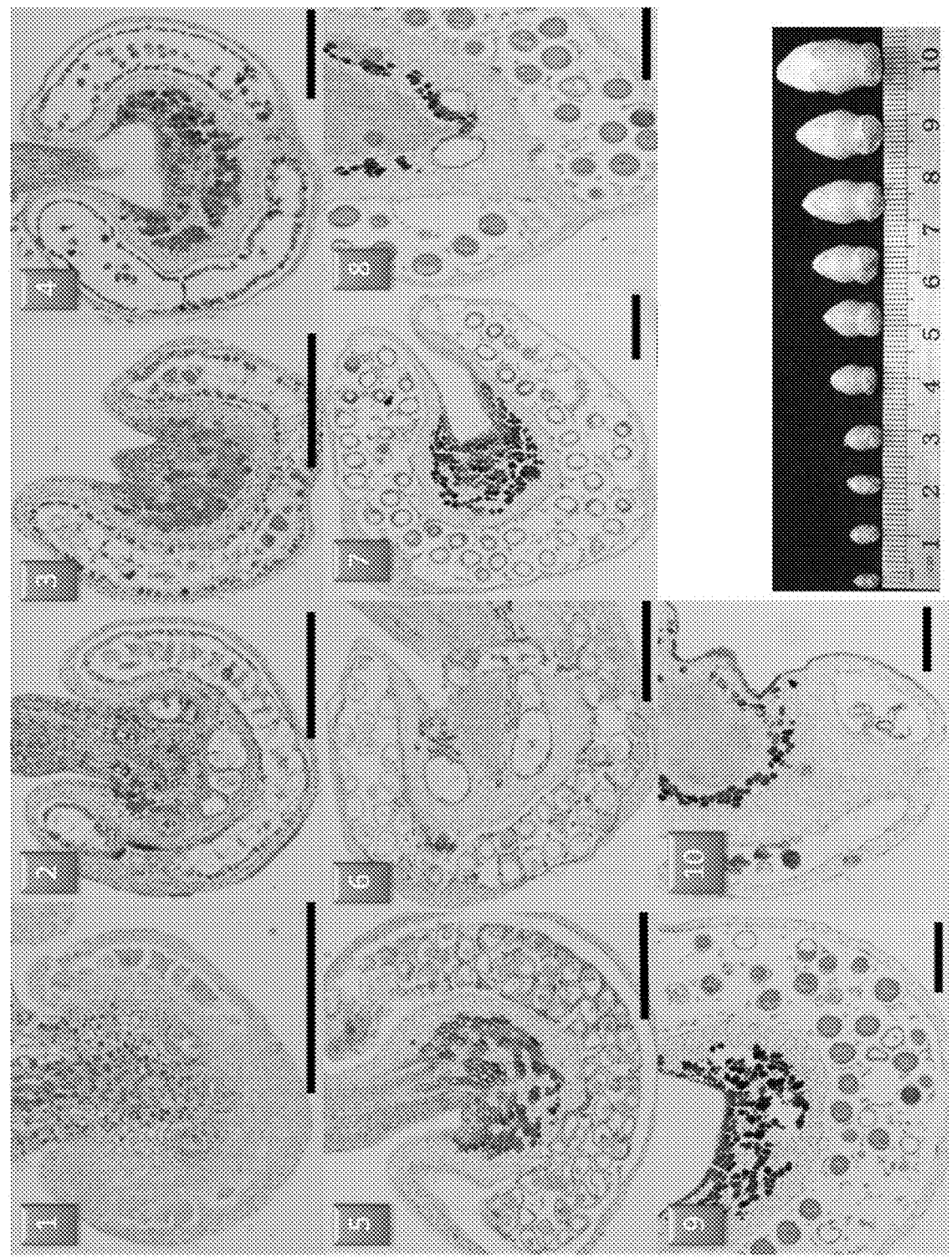
FIG. 4 shows a paraffin section of anther development of PSM1. The anther sections of 1-10 correspond to the bud stages of different sizes of cotton in the lower right corner; the length of the scale is 200 microns; and 10 is the cotton bud 2 days before blooming. 1-9 show that the tapetal layer is not degraded in advance, and it can still provide organic matters for pollen grains to increase the cytoplasmic concentration in 8-9 stages, and the 10 stage is 2 days before flowering, it can be seen that the pollen grains suddenly aborted, leaving only residual pollen walls.
Figure 5:
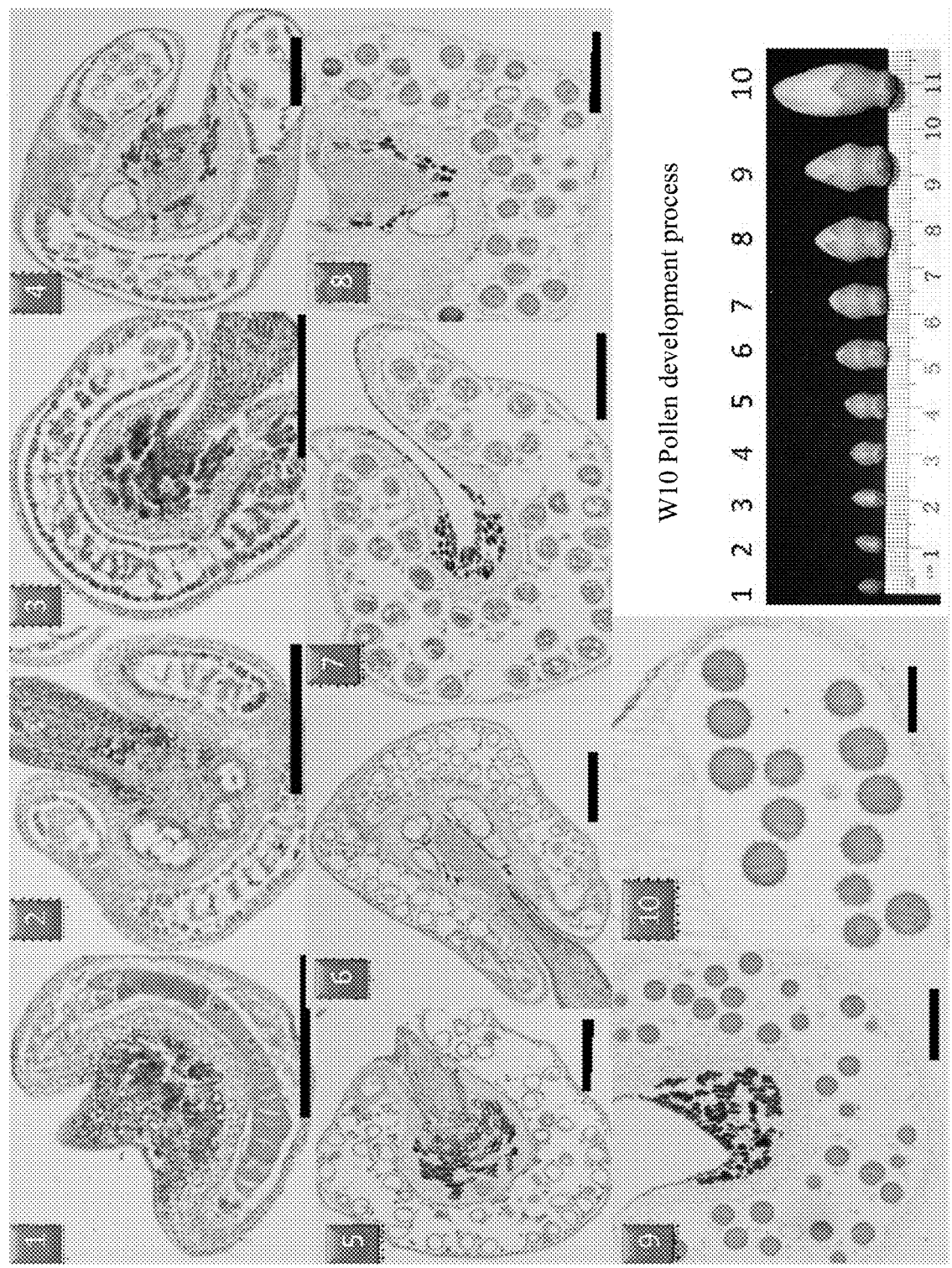
FIG. 5 shows a paraffin section of anther development of W10. The anther sections of 1-10 correspond to the bud stages of different sizes of cotton in the lower right corner; the length of the scale is 200 microns; and 10 is the cotton bud 2 days before blooming. The 10 stage is 2 days before flowering, and mature cotton pollen grains can be seen at this stage.

5. The abortion of pollen grains of PSM1 occurred at the mid-late uninucleate stage in the development of pollen grains (the 6 in FIG. 4 refers to the mid-late uninucleate stage). This was because that the tapetal layer could not supplement outer layer materials for filling to the outer layer of the pollen wall, and the pollen cytoplasm decreased or disappeared 1-2 days before flowering, so that the pollen grains could not mature finally and causes sterility, rather than due to the in advance degrading of the tapetal layer (FIGS. 4 and 5).

6. The normal fertile cotton and PSM1 mutants were subjected to reciprocal crossing, and their F1 generation showed normal fertility and normal leaf color. Therefore, both the photoperiod-sensitive sterility and yellowing traits of PSM1 were controlled by recessive nuclear genes. The ratio of fertile plants to sterile plants in the $F_2$ generation was close to 3:1 (it could be inferred that the photoperiod-sensitive male sterile trait of PSM1 was controlled by a recessive single gene). All of the fertile plants were not yellowed, and the ratio of yellowed plants to non-yellowed plants in the sterile plants was 15-40:1, showing incomplete linkage. The specific genetic situation requires further experimental evidence of a large-scale population. Since the photoperiod-sensitive male sterility and yellowing traits of PSM1 were incompletely linked, photoperiod-sensitive genic sterility materials with different yellowing degrees (such as PSM2 and PSM3 in FIG. 1) or photoperiod-sensitive sterility materials bearing no marker traits (such as PSM4 in FIG. 1) could be bred.

7. The PSM1 mutants were hybridized with normal fertile cotton, and the sterile plants separated from the hybridization progenies had the same photoperiod-sensitive sterility characteristic as the PSM1 mutant and can be free of similar yellowing markers.

Example 2. Obtaining of PSM1 Seeds

1) The seeds were sowed in Sanya, Hainan, and could grow all year round. Selfing was conducted during the period in which there was pollen from late November to February of the following year, such that PSM1 selfing seeds could be harvested to complete the seed breeding;

2) the seeds were sowed in other areas that were suitable for cotton growth, and selfing was conducted in the period when the hours of sunshine was less than 11.5 hours, so as to harvest PSM1 seeds;

3) the seeds were planted under the condition of manually controlled illumination time so that the daily hours of sunshine perceived by PSM1 was less than 11.5 hours, the fertility was restored, and selfing was carried out to harvest PSM1 seeds.

Example 3: Planting PSM1 in a Field of Anyang, Henan

I. Sowing Seeds

The seeds of PSM1 could be sowed according to the normal sowing procedure of cotton in production. When the seeds were sowed directly in middle and late April in a field of Anyang, PSM1 showed yellowing of prophyll (the first and second euphyllas), and slightly yellow cotyledons. Thereafter, the subsequent euphyllas were green. PSM2, PSM3 and PSM4 showed no yellowing of the prophyll.

II. Growth and Development

1. The plants were planted in Anyang, Henan, with the growth and development laws being similar to those of W10, and the growth period was basically the same as that of W10.

2. In Anyang, Henan, there was no normal pollen in the whole growing period of cotton. Anthers could not dehisce, and selfing and boll setting could not occur, but hybridization boll setting could occur.

3. The plants could be used for hybrid seed production and crossbreeding in Anyang, Henan.

Example 4: Planting PSM1 in Sanya, Hainan

1. It could be sown all year round in Sanya, Hainan. When sowed in a field, PSM1 had the yellowing phenomenon, and the growth rate of PSM1 in the field was about ⅔ of that of W10.

2. There was no obvious difference in phenotypes between PSM1 and W10 plants planted in a greenhouse of Sanya, Hainan.

3. Under natural light conditions, the flowers that bloomed after the late November to the end of February of the following year have normal pollen. The anthers were dehiscent and shed pollen naturally, such that selfing and boll setting could occur. The anthers did not dehisce or couldn't shed pollen at other times, and thus only hybrid seed production could be done with the pollen provided by normal fertile cotton materials, and hybrid seeds were harvested.

Example 5: Breeding Photoperiod-Sensitive Male Sterile Line Using PSM1

1. PSM1 was used as the male parent or female parent to hybridize with other fertile cotton materials to harvest hybrids of F1 generation.

2. The $F_1$ generation was planted, and subjected to selfing. The $F_2$ generation was harvested to separate the photoperiod-sensitive male sterile plants with the photoperiod trait of PSM1.

3. The photoperiod-sensitive male sterile plants separated from the hybrid progenies were subjected to selfing or backcrossing for multiple generations under appropriate illumination conditions, such that a photoperiod-sensitive male sterile line with the same photoperiod response as that of PSM1 could be bred for improvement of the sterile line.

Example 6: Hybrid Breeding by Using PSM1

1. PSM1 was planted as the female parent under the illumination condition that PSM1 was presented as male sterile (the hours of sunshine was greater than 11.5 h).

2. The fertile cotton materials were selected as the male parent.

3. The pollen of the male parent was given to the female parent PSM1 by artificial or insect auxiliary methods, and hybrid seeds on the PSM1 plants were harvested.

4. Due to the male sterility of PSM1, the steps of artificial emasculation could be eliminated, a great deal of manpower could be saved, and the cost of seed production cost be reduced. This could be used for mass production of hybrid cotton.

Example 7: Breeding Hybrid Cotton Using a New Photoperiod-Sensitive Male Sterile Line Bred from PSM1

1. Improved sterile lines with the photoperiod-sensitive sterility of PSM1 were bred using the method of example 5.
2. Hybrid combinations were configured by using the method of Example 6, so as to breed hybrid cotton.

Example 8: Breeding Improved Sterile Line Material by Using PSM1 or the Method of Example 5, Establishing a Mass Selection-Mass Crossing System to Breeding a New Variety, the Specific Implementation Steps were as Follows 1) PSM1 or the photoperiod-sensitive male sterile line material bred in Example 5 was selected, and then it and other fertile upland cotton, Gossypium barbadense L. and the like materials were subjected to mixed planting in an area where PSM1 could show the photoperiod-sensitive male sterility.
2) When PSM1 was used, the male sterile plants could be determined according to the prophyll yellowing at the seedling stage, and sterile plants were distributed evenly in the field as much as possible during Seedling thinning and marked well.
3) Natural pollination or insect-assisted or artificial-assisted pollination was conducted during the flowering and boll setting stage, so as to realize mixed crossing.
4) the seeds on the individual photoperiod-sensitive male sterile plants were harvested, wherein the seeds on the individual photoperiod-sensitive male sterile plants were mixed hybrid seeds.
(5) The hybrid seeds harvested from the photoperiod-sensitive male sterile plants were planted, subjected to selfing and harvested as a mixture.
6) the harvested seed mixture was planted in an area where PSM1 showed the photoperiod-sensitive male sterility, and the photoperiod-sensitive male sterile plants were marked. Natural pollination or artificial-assisted pollination was conducted during the flowering and boll setting stage, so as to continue the mixed crossing to obtain seeds of mixed crossing.
7) The seeds on the photoperiod-sensitive male sterile line were harvested. The steps 4), 5) and 6) were repeated to realize multiple times of mixed crossing.
8) In the steps 4), 5) and 6), the individual fertile plants could be utilized for the cotton cross-breeding and system selection as breeding materials. Excellent individual plants were selected to enter the selective breeding pathway, and excellent varieties were bred through multiple generations of selfings and selective breeding, so as to realize the breeding of new varieties.
9) In the steps 4), 5) and 6), individual fertile plants with excellent traits and uniform phenotypes could be selected and mixed to serve as mixed line materials, so as to breed mixed line varieties.
10) In steps 6) and 7), other cotton materials could be added to the mixed-crossing population, and then the population was subjected to mixed planting to introduce new breeding materials and expand the genetic background of the mixed-crossing population.

Example 9. Breeding New Varieties Using the Photoperiod-Sensitive Genic Male Sterile Lines The hybrid seeds obtained by the methods of Examples 4, 5, 6, 7 and 8 be utilized for the cotton systematic breeding, so as to breed new photoperiod-sensitive male sterile lines and new varieties through selection of multiple generations.

INDUSTRIAL APPLICATION

In the present invention, hypocotyls of aseptic seedlings of a high-differentiation-rate strain W10 that was suitable for cotton tissue culture and was screened out from CRI24 were taken as explants, and subjected to tissue culture to obtain a large number of regenerated plants (ZL200610089439.1), from which the mutants were selected. The PSM1 (Photoperiod-sensitive genic male Sterility Mutant of cotton) mutant found in the progenies of cotton regenerated plants in 2012 was obtained through tissue culture. The phenotype of PSM1 was different from each of those of the reported cotton virescent mutants, and belonged to a new type. Sowing was conducted in the normal sowing period of cotton in the middle and late April in Anyang, Henan. The cotyledons of PSM1 after emergence were slightly yellower and larger than those of W10. The first and second euphyllas were yellowed. That was, the prophyll was yellowed and the yellowing could not be recovered. Thereafter, the euphyllas were all green without the yellowing phenomenon. In Anyang, no yellowing phenomenon was observed when seedling was conducted in a greenhouse or seed sowing was conducted in late May. Direct sowing was conducted in a field of Sanya, Hainan, and the plants were presented with whole plant yellowing. When the seeds were sowed in a greenhouse of Hainan, the plants had no yellowing phenomenon. Therefore, according to preliminary tests, it was believed that yellowing is related to light intensity and temperature. The plants were easily yellowed under high light intensity and low temperature conditions. The yellowing of new leaves was light, the yellowing of old leaves was heavy, and the yellowing of leaves at shaded portions was light. PSM1 was planted in a greenhouse of the Damao HNBM (Hainan National Breeding and Multiplication) base of the Institute of Cotton Research of Chinese Academy of Agricultural Sciences in Jiyang district of Sanya and grown for 2 consecutive years to observe the fertility change time. It was found that pollen of PSM1 began to appear from November 15 to 25, and selfing and boll setting could occur to enter the fertile growth stage. From February 20 to March 1, the phenomenon of non-dehiscent anther and selfing without boll setting began to appear, and thus the male sterility stage was entered. The fertility change period of PSM1 should be about 11.5-12 hours. It was determined that the plants showed male sterility under the illumination condition that the hours of sunshine was greater than 12 hours; the plants began to restore the fertility when the hours of sunshine was less than 11.5 hours; and the period during which the hours of sunshine was 11.5-12 hours is the fertility change stage. The females were fertile throughout the year and were not affected by the photoperiod. The photoperiod-sensitive male sterility and yellowing traits were incompletely linked. Photoperiod-sensitive male sterile line materials bearing no yellowing marker could be selected, such as the photoperiod-sensitive male sterile line PSM4 that had no yellowing marker in both the field of Anyang and the field of Hainan, and the photoperiod-sensitive male sterile lines PSM2 and PSM3 that had no yellowing marker when planted in the field of Anyang and had a light yellowing marker when planted in the field of Hainan. Since all of the cotton regions in China, such as the Yangtze River planting areas, the Yellow River planting areas and the Northwest inland planting areas, had the hours of sunshine of greater than 12 hours during the cotton growing season, all of the cotton regions in China were suitable areas for hybrid seed production of it. At the same time, the flower stigma of the cotton sterile material provided by the present invention was the same as that of the normal cotton. No elongation of the flower stigma occurred, and the anther was full and not wizened, so that the cotton sterile material is very suitable for the hybrid seed production mode of insect (such as bees and the like) assisted pollination. Therefore, the photoperiod-sensitive genic male sterility mutant of cotton provided by the present invention has very great significance in cotton heterosis utilization, hybrid seed production and breeding of cotton.

What is claimed is:

1. A cotton line named upland cotton line PSM1 (*Gossypium hirsutum* L.) that is self-breeding offspring of a mutant plant obtained through genetic variation caused by somatic tissue culture regeneration of said upland cotton strain W10 and having a preservation number CGMCC No. 14613 in the China General Microbiological Culture Collection Center, wherein said cotton line comprises:
   (a) a photoperiod-sensitive male sterility trait that is a mutant trait obtained through genetic variation caused by somatic tissue culture regeneration of an upland cotton plant strain W10,
   wherein said photoperiod-sensitive male sterility trait is influenced by the photoperiod such that said photoperiod-sensitive male sterility trait (i) shows normal male fertility when the daily illumination time is less than 11.5 h, (ii) shows male sterility when the daily illumination time is greater than 12 h, and (iii) is in a fertility change period when the daily illumination time is in the range of 11.5-12 h; and
   (b) a prophyll yellowing selection trait that is affected by temperature.

2. The cotton line of claim 1, wherein said prophyll yellowing selection trait is affected illumination intensity.

3. The cotton line of claim 2, wherein said photoperiod-sensitive male sterility trait is a recessive single gene; and said prophyll yellowing trait is incompletely linked with said photoperiod-sensitive male sterility trait.

4. The cotton line of claim 1, wherein said cotton line is an improved cotton material in which said prophyll yellowing selection trait is modified into other selection markers or no selection markers, but said photoperiod-sensitive male sterile trait can still be maintained.

5. A method for producing a hybrid cotton seed, said method comprising: crossbreeding the cotton line of claim 1 having a photoperiod-sensitive male sterile trait as a female parent with a fertile cotton material as a male parent to produce said hybrid cotton seed.

6. The method according to claim 5 further comprising the steps of:
   crossbreeding said hybrid seed; and
   selecting (i) a photoperiod-sensitive male sterile line, (ii) a new breed of cotton variety, or (iii) a combination thereof.

7. The method according to claim 5, wherein said method further comprises hybridizing said cotton line comprising said photoperiod-sensitive male sterility trait with another cotton material to obtain a F1 generation, and
   (i) selecting cotton materials with a photoperiod-sensitive male sterile trait from the offspring population of the F1 generation; or
   (ii) (a) subjecting cotton materials with the photoperiod-sensitive male sterile trait selected from the offspring population of the F1 generation to one or more selfings, and
       (b) selecting the cotton materials with the photoperiod-sensitive genic male sterile trait from the offspring of selfing; or
   (iii) (a) transferring a photoperiod-sensitive male sterile trait of said cotton line or said cotton material to another cotton material through backcrossing, and
       (b) selecting said another cotton material with said photoperiod-sensitive male sterile trait from an offspring of backcrossing.

8. An upland cotton line PSM1 (*Gossypium hirsutum* L.) having a preservation number of CGMCC No. 14613 in the China General Microbiological Culture Collection Center.

9. The upland cotton line PSM1 (*Gossypium hirsutum* L.) of claim 8, wherein said cotton line is a germinable seed.

* * * * *